(12) United States Patent
Meyerhoff et al.

(10) Patent No.: US 6,815,425 B1
(45) Date of Patent: Nov. 9, 2004

(54) PHARMACEUTICAL COMPOSITION CONTAINING PGLU-GLU-PRO-NH$^2$ AND METHOD FOR TREATING DISEASES AND INJURIES TO THE BRAIN, SPINAL CORD AND RETINA USING SAME

(75) Inventors: James L. Meyerhoff, Silver Spring, MD (US); Michael L. Koenig, Silver Spring, MD (US); Joseph B. Long, Clarksville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 8 days.

(21) Appl. No.: 09/692,938

(22) Filed: Oct. 20, 2000

Related U.S. Application Data
(60) Provisional application No. 60/160,972, filed on Oct. 22, 1999.

(51) Int. Cl.$^7$ .......................... A61K 38/06; C07K 5/08
(52) U.S. Cl. ..................... 514/18; 514/579; 514/638; 530/331; 564/300
(58) Field of Search .................. 514/18, 579, 638, 514/646; 530/331; 564/300

(56) References Cited

U.S. PATENT DOCUMENTS

| | | | |
|---|---|---|---|
| 4,609,365 A | 9/1986 | Eberle | 514/18 |
| 4,906,614 A | 3/1990 | Giertz et al. | 514/18 |
| 5,508,305 A | 4/1996 | Carney | 514/517 |

FOREIGN PATENT DOCUMENTS

| WO | WO 00/64440 | 4/1999 |
|---|---|---|

OTHER PUBLICATIONS

NINDS Amyotrophic Lateral Sclerosis Information Page. Available online, website: <www.ninds.nih.gov/health_and_medical/disorders/amyotrophiclateralsclerosis_doc.htm>. Last Updated: Jul. 2001. Accessed on Mar. 17, 2002.*
Amytrophic Lateral Sclerosis Fact Sheet. Available online, website: <www.ninds.nih.gov/health_and_medical/pubs/als.htm>. Accessed on Mar. 17, 2002.*
Parkin's Disease–Hope Through Research. Available online, website: <www.ninds.nih.gov/health_and_medical/pubs/parkinson_disease_htr.htm>. Accessed on Mar. 17, 2002.*
Cremades et al. 'The thyrotropin–releasing hormone–like peptides pGlu–Phe–Pro amide and pGlu–Glu–Pro amide increase plasma triiodothyronine levels in the mouse; the activity is sensitive to testosterone', European Journal of Pharmacology, vol. 358, p. 63.*
Patel et al. 'Pharmacotherapy of Cognative Impairment in Alzhemier's Disease: A review', J. Geriatr. Psychiatry Neurol. vol. 8, pp. 81–95. 1995.*

Kuroda, S., et al. Neuroprotective Effects of a Novel Nitrone, NXY–059, after transient focal cerebral ischemia in the rat, Journal of Cerebral Blood Flow and Metabolism, 19:778–787 (1999).
Cheng, H., et al., Distribution of spin trapping compounds in rat blood and brain in vivo microdialysis determination, Free Radical Biology and Medicine, vol. 14, pp 243–250 (1993).
Cao, X., et al., Alpha–Phenyl–tert–butyl–nitrone reduces cortical infarct and edema in rats subjected to focal ischemia, Brain REsearch 644 (1994) 267–272.
Kuroda, S., et al,, Delayed treatment with Alpha–Phenyl–n–tert–butyl nitrone (PBN) attenuates secondary mitochondrial dysfunction after transient focal cerebral ischemia in the rat, Neurobiology of Disease 3, (1996) 148–157.
Schulz, J., et al., Improved therapeutic window for treatment of histotoxic hypoxia with a free radical spin trap, Journal of Cerebral Blood Flow and Metabolism, 15: 948–952 (1995).
Schulz, J. et al., Involvement of free radicals in excitotoxicity in vivo, Journal of Neurochemistry, vol. 64, No. 5 (1995) p 2239–2247.
Thomas C., et al., Characterization of the radical trapping activity of a novel series of cyclic nitrone spin traps, J. of Biological Chemistry, vol. 271, No. 6, (Feb. 9, 1996) p 3097–3104.
Thomas C., et al., Radical Trapping and inhibition of iron–dependent CNS damage by cyclic nitrone spin traps, J. of Neurochemistry, vol. 68, No. 3, (1997) p 1173–1182.
Zeevalk, G., et al, Role of oxidative stress and the glutathione system in loss of dopamine neurons due to impairment of energy metabolism, J. of Neurochemistry vol. 70, No. 4 (1998) p 1421–1430.
Pekary, Eugene, et al., Electroconvulsive seizures modulate levels of thyrotropin releasing hormone and related peptides in rat hypothalamus, cingulate and lateral cerebelium, Brain Research 884, (2000) 174–183.
Haseloff, P. et al, Cytotoxicity of spin trapping compounds, FEBS Letters 418 (1997) 73–75.
Koenig, M L et al. "Neuroprotection by the TRH–like peptide pGLU–GLU–PERO–NH$_2$ (EEP)." Society for Neuroscience Abstracts, vol. 24, No. 1–2, 1998, p. 459.
Koenig, et al., In vitro neuroprotection against glutamate–induced toxicity by pGlu–Glu–Pro–NH$_2$ (EEP), Peptides 22 (2001) 2091–2097.
Faden, Effects of TRH on Blood Flow, Circulatory Shock, and CNS Injury, Annals New York Academy of Sciences, p. 285–387, (1989).
Marangell, Effects of Intrathecal Thyrotropin–Releasing Hormone (Protirelin) in Refractory Depressed Patients, Arch Gen Psychiatry/vol. 54, Mar. 1997.

* cited by examiner

Primary Examiner—Brenda Brumback
Assistant Examiner—Anish Gupta
(74) Attorney, Agent, or Firm—Elizabeth Arwine

(57) ABSTRACT

A nueroprotectant composition wherein the active ingredient is pGLU-GLU-PRO-NH$^2$ or a combination of pGLU-GLU-PRO-NH$^2$ (EEP) and N-tert-Butyl-α-(2-sulfophenyl)nitrone (SPBN) or other nitrone. A method of treating and preventing diseases and injuries of the brain, spinal cord and retina is also presented by administering the endogenous tripeptide EEP to a subject as a neuroprotectant or by administering EEP in combination with SPBN or other nitrone.

7 Claims, No Drawings

PHARMACEUTICAL COMPOSITION CONTAINING PGLU-GLU-PRO-NH$^2$ AND METHOD FOR TREATING DISEASES AND INJURIES TO THE BRAIN, SPINAL CORD AND RETINA USING SAME

FIELD OF THE INVENTION

This application claims the benefit of the filing date of U.S. provisional application serial No. 60/160,972 filed Oct. 22, 1999.

The present invention is directed to a neuroprotectant composition wherein the active ingredient is pGLU-GLU-PRO-NH$_2$ or a combination of pGLU-GLU-PRO-NH$_2$ (EEP) and N-tert-Butyl-α-(2-sulfophenyl)nitrone (SPBN). The present invention is also directed to a method of treating and preventing diseases and injuries of the brain, spinal cord and retina by administering the endogenous tripeptide EEP to a subject as a neuroprotectant or by administering EEP in combination with SPBN or other nitrone.

BACKGROUND OF THE INVENTION

Twenty percent of all combat wounds involve the head. Penetrating head wound have a greater than 50% risk of developing posttraumatic epilepsy. Closed head injuries are more prevalent in the military than in the civilian community, and certain groups (e.g. paratroopers) are at special risk for both head and spinal injury. Among Naval personnel, certain occupational specialties are at increased risk for air gas embolism or decompression sickness (DCS), and the major neurological complication of either is spinal cord damage. There is also risk of oxygen toxicity-induced seizures. Severe head injury, or cerebral ischemia, is associated with a high mortality rate and poor functional outcome. Despite extensive clinical and experimental research, there are no well-defined therapies for these conditions. There are very few available treatments for brain injury today and the gradual progressive biochemical changes which occur after head trauma can lead to the evolution of permanent neuronal damage.

Further, personnel in all branches of the U.S. military are at risk for laser injury to the retina. Laser energy could be deliberately directed at the cockpit of U.S. military aircraft (airplanes and/or helicopters) with the intent of impairing the vision of pilots and/or crews (door gunners or medics). The adverse effects on the retina may range from transient impairment which can impact operational performance, to lasting disability or blindness. Reconnaissance troops and TOW missile operators are also at risk. Other potential sources of laser-induced retinal injury include exposure to laser targeting and ranging devices. A common source of laser-induced retinal injury in soldiers is the hand held neodymium (Nd:YAG) laser target designator (range finder), which operates at a wavelength of 1064 nanometers. Ruby lasers operating at a wavelength of 694.3 nm have also been used in military range finders and represent an additional potential source of retinal damage. The normal function of the lens, focussing light onto the retina, also serves to concentrate incident laser energy, when exposure occurs. While the magnifying effect of the human lens on intraocular laser energy is large as much as 10,000 fold—the amplification in the case of a soldier using binoculars could reach as much as $10^6$. The amount of laser energy reaching the retina is also directly related to pupil diameter. Thus, soldiers are at greater risk under dark-adapted conditions. Finally, the location of the laser-induced lesion is clinically very important, with foveal location being the most severe. Laser injuries near the fovea present a risk of penumbral spread over time to include the fovea.

Naval personnel are also at risk for decompression sickness (DCS) in at least two operational scenarios: (1) SEALS on extended underwater operations; (2) Submariners, during emergency evacuation, of crew from a submarine disabled on the continental shelf. Navy SEAL operations often require prolonged (e.g. up to 10 hours) dives at shallow depth (e.g. 40–60 feet), breathing high concentration oxygen, sometimes followed by brief excursions at greater depth. These personnel are at risk for air embolism, which can cause spinal injury, similar to that seen in decompression sickness (DCS), and oxygen toxicity-induced seizures.

Submarines could become disabled (DISSUB) on the ocean floor, requiring emergency evacuation of the crew. In this scenario, arrival of a rescue ship could take days, during which time crews in a disabled submarine could be exposed to hyperbaric conditions. To accomplish a DISSUB rescue expeditiously, a submersible rescue vessel would transport the crew to the surface in groups, potentially without decompression. Once on the surface, crew members may be required to wait for access to treatment in a limited-capacity recompression chamber on the surface. Because of the delay in treatment, some personnel might be at significant risk for neurological complications of DCS. Spinal cord injury is a relatively common sequela of DCS; recompression treatment is not always successful and if delayed, prognosis for recovery is poor. The prolonged delay before submarine crews might be brought to the surface, provides a significant window of opportunity for administration of a safe, well-tolerated prophylactic treatment to mitigate risk and severity of possible neurological complications of DCS.

Leading causes of blindness include: age-related macular degeneration (AMD), diabetic retinopathy (DR), glaucoma and cataracts. The prevalence of diabetes in North America is estimated to reach almost 17 million by the year 2000. In cases of insulin-dependent diabetes mellitus (IDDM) with onset before age 30, the average prevalence of proliferative retinopathy (DPR) is estimated at 23%. In IDDM of more than 30 years duration, however, the incidence of DPR rises to 70%. DPR is the leading cause of new cases of blindness in the U.S., accounting for 12% of new cases annually. The prevalence of AMD increases from over 2% in the age group of 60–64 years to over 25% in the 75–80 year group. It is estimated that the prevalence of glaucoma in the United States will be 2.9 million by the year 2000, and that over 130,000 will have been blinded by this disease.

A major pathological mechanism in both AMD and DPR is retinal neovascularization. The mechanisms of DPR include excessive retinal vascular permeability, edema, ischemia and the principal causes of loss of vision are hemorrhage into the vitreous and/or retinal detachment. The only effective treatment known for either AMD or DPR is coagulation via exposure to focussed laser irradiation (Vinding, 1995). Laser photocoagulation in a grid pattern is an effective treatment for the macular edema seen in diabetic retinopathy, as well as the neovascularization.

Unfortunately, exposure of the retina to laser energy, whether therapeutic or accidental results in formation of scotoma and visual impairment. Even after therapeutic exposures, there may be immediate and progressive visual impairment, due to destruction of normal retinal cellular elements with subsequent spread of injury to adjacent retinal tissue. In one study, progressive enlargement of laser scars was found in 11 of 203 patients with diabetic retinopathy treated via laser photocoagulation in a grid pattern.

Since the retina contains neurons and axons and is part of the central nervous system, recent advances in understanding of mechanisms of neurotoxicity apply, as do the related advances in research on neuroprotective agents. Ganglion cells are the output neurons of the retina and axons projecting from these cells form the optic nerve and project to the lateral geniculate nucleus of the brain. In one study, 12 hours after laser exposure, ganglion cells in monkey retina were liquefied. Ganglion cells are also destroyed in glaucoma, and continue to perish even after institution of standard glaucoma therapy.

Currently, post-injury treatment of spinal injury is most likely to include administration of the steroid methylprednisolone for 24 or 48 hours to reduce swelling and inflammation. In patients with accident-related acute spinal cord injury, clinical outcome at six months was improved in those receiving treatment with methyl prednisolone within eight hours of injury, compared to placebo-treated (Bracken et al., 1990 & 1997). Unfortunately, there is some evidence that glucocorticoids (GCs) can exacerbate the excitotoxic phase of neural injury. Postulated mechanisms of GC-mediated synergy with excitotoxic effects of glutamic acid (GLU) include: (1) GCs inhibition of reuptake inactivation of synaptic GLU, thereby increasing synaptic GLU levels; (2) GCs inhibition of calcium efflux from the postsynaptic neuron (McEwen & Sapolsky, 1995). In fact, methylprednisolone has recently been proven to exacerbate laser-induced lesions of the retina (Schuschereba et al., 1997). Other possible candidates, such as drugs which block the effects of glutamate at its NMDA receptor or the associated ion channel are associated with unacceptable behavioral toxicity (Tricklebank et al., 1989).

Some prior compounds have shown an ability to have some neuroprotective capabilities. For instance, thyrotropin-releasing hormone (TRH), is a tripeptide comprised of the amino acids pyroglutamate-histidine-proline-amide. TRH has been shown to be neuroprotective, analeptic, anticonvulsant and antidepressive. TRH was initially recognized as a peptide released by the brain to stimulate secretion of thyroid-stimulating hormone from the pituitary gland. Subsequently, TRH was identified in many brain regions and associated with numerous physiological functions. When injected, TRH was found to have many behavioral effects, including, analeptic, anticonvulsant and antidepressant (Sato et al., 1984; Sattin et al., 1987). Its in vivo neuroprotective effects in animal models of both brain and spinal cord injury have been reviewed by Faden et al. (1989). The early promise of TRH, however, has not been realized because it has properties which severely limit its clinical potential. Because injected TRH is rapidly hydrolyzed by the enzyme pyroglutamylpeptidase II which is found in blood (Cockle, et al., 1994; Klootwijk et al., 1997), its bioavailability and hence its clinical potential has been severely limited. Another limitation on therapeutic use of TRH might be potential for excessive activation of the thyroid gland.

TRH is not a suitable neuroprotectant because it is hydrolyzed by serum enzyme thyroliberinase which limits its bioavailability. Also TRH elevates plasma levels of thyroid hormone, which could potentially be problematic.

Other neuroprotectants are nitrone based free radical traps such as α-Phenyl-N-tert-butylnitrone (PBN) which offer an ROS scavenging mechanism which differes from vitamin E and other endogenous compounds (*Althaus et al., 1998). The nitrones react covalently with ROS to form stable nitroxides and as such have been used to measure ROS. They have also been shown to be neuroprotective against glutamate-induced toxicity in cultured neurons (Zeevalk et al. 1998) as well as in several rodent models of cerebral ischemia, including transient global ischemia (Oliver et al., 1990), transient (ZHO et al., 1994, Folbergrova et al., 1995) and permanent [100 mg/kg 30 mim pre-ischemia; repeated at intervals after injury] (Cao & Phillis, 1994) occlusion of the middle cerebral artery (Read et al., 1999). Unfortunately, PBN caused significant toxicity at high doses (Haseloff et al., 1997) and is thus, unsuitable for serious consideration as a neuroprotectant.

SPBN (N-tert-Butyl-α-(2-sulfophenyl)nitrone) is also a neuroprotectant without significant toxicity and studies have shown that SPBN is protective against striatal injections of NMDA, kainic acid, AMPA, MPP+, 3-acetyl pyridine and malonate, decreasing the volume of the lesions induced by those toxins (Schulz et al., 1995), as well as decreasing malonate induced formation of ROS (Schulz et al., 1995).

Finally, another nitrone NXY-059, was shown to be effective in both tempory (Kuroda et al., 1999) and permanent focal ischemia models in the rat, and was effective when given 3 hours (Kuroda et al,1999) or even 5 hours (Maples et al., 1999) after start of recirculation in the former. In preliminary studies, NXY-059, administered either 15 min prior or 30 min post TBI was effective in decreasing volume of necrosis in the controlled cortical impact model (Cheng, et al., 1999). This compound is currently being developed for treatment of stroke by Centaur Pharmaceuticals and Astra/Zeneca.

Since no proven effective therapy for treating diseases and injuries to the brain, spinal cord and retina, are yet known, the importance of finding such therapeutic neuroprotectant is self-evident. What is needed is an effective neuroprotectant which has clinical use across a wide spectrum of injuries and diseases. What is also needed is a neuroprotectant which is not rapidly hydrolyzed in the blood and which is not toxic at low or high doses. Therefore, the object of the invention is to provide such a neuroprotectant to fill the current needs.

Briefly, this and other objects of the present invention as hereinafter will become more readily apparent.

SUMMARY OF THE INVENTION

The invention solves the above problems associated with known neuroprotectants by providing a neuroprotectant composition wherein the active ingredient is pGLU-GLU-PRO-$NH^2$ (EEP) or a combination of pGLU-GLU-PRO-$NH_2$ (EEP) and N-tert-Butyl-α-(2-sulfophenyl)nitrone (SPBN). The present invention is also directed to a method of treating and preventing diseases and injuries of the brain, spinal cord and retina by administering the endogenous tripeptide EEP to a subject as a neuroprotectant or by administering EEP in combination with SPBN or other nitrone.

DETAILED DESCRIPTION

The inventors have found that the endogenous tripeptide, EEP or EEP and SPBN and other nitrone (EEP treatment) is effective as a treatment for a wide range of injuries and diseases of the brain and spinal cord in the military and civilian sector. EEP treatment can be given at the first sign of spinal injury in service members such as divers, seals and submariners, as well as paratroopers, sport divers and victims of automobile accidents. EEP treatment can also be given for degenerative diseases of the spinal cord, such as amyotrophic lateral sclerosis and multiple sclerosis; neuronal degeneration due to traumatic brain injury, stroke; and degenerative brain diseases such as Parkinson's, Huntington's and Alzheimer's.

This invention can also prevent or minimize DCS-induced spinal cord injury, as well as injury due to blast overpressure, or blunt and/or penetrating trauma. EEP treatment can be made available to combat medics in an appropriate delivery mode to achieve high retinal concentrations of EEP rapidly, even when delivered to a casualty at a far-forward echelon. Pre-treatment of DPR patients with EEP prior to laser retinal therapy will limit the penumbral spread of laser injury beyond the intended zones of therapy, thus preventing enlargement of laser scars. Further, chronic treatment with EEP of patents would also slow the progression of glaucoma, treat temporal arteritis or retinitis pigmentosa and serve as adjuvant therapy before, during and after cataract surgery or retinal photocoagulation treatments for either age-related macular degeneration or diabetic retinopathy.

Additional uses for EEP treatment include minimizing collateral damage before, during and after therapeutic exposure to ionizing radiation for malignacies, especially of the head and neck. Protection against exposure to ionizing radiation and/or high-energy particles or plasmas such as iron-26. Protection against retinal damage during eye surgery or in occupational exposures such as in welders and firefighters.

EEP is found in brain, pituitary and reproductive tissues of rodents, and in serum of both rat and man. Although EEP has a structure very similar to that of thyrotropin-releasing hormone (TRH), it has both similarities and important differences in physiological effects. The three amino acid structure of EEP is pyroglutarnate-glutamate-proline-amide—a structure very similar to that of thyrotropin-releasing hormone (TRH). Thyrotropin-releasing hormone (TRH), is a tripeptide comprised of the amino acids pyroglutamate-histidine-proline-amide (EHP), differing from EEP only in having histidine, rather than glutamate in the number 2 position.

Along with the marked structural similarities with TRH, EEP has some similarities in physiological effects. For example, like TRH, if administered to rats, it increases locomotor activity, and decreases immobility in the Porsolt swim test (Lloyd et al., 1997). Regional brain levels of EEP are markedly increased by electroconvulsive shock (Pekary et al., 1997), another similarity with TRH (Sattin et al., 1987; Meyerhoff et al., 1990). But there are also significant contrasts between the two peptides. Regional brain levels of EEP tend to be consistently higher than levels of TRH in the same region. For example, a comparison of reported levels of EEP vs. TRH (in ng/g wet weight) are 2.31 vs 1.45 in the amygdala and 0.96 vs. 0.3 in cortex (Pekary et al., 1998). EEP has been reported to be more stable than TRH in follicular fluid (Ashworth et al., 1991). Moreover, in marked contrast to TRH, EEP is reportedly not degraded at all in human serum (Cockle et al., 1994; Klootwijk et al., 1997), and therefore its bioavailability is far superior to that of TRH. For example, after intrapentoneal injection (1.0 mg/kg) in rats, regional brain levels of EEP increase as follows: in amygdala, 7 fold; in cortex, 14 fold; in the medulla, 4 fold; and in the hypothalamus, 2 fold. In addition, levels in the pituitary increased 11 fold and, especially relevant to proposed uses in ophthalmology, levels in the eye increased Over one hundred fold (Pekary et al., 1998). Further, like TRH, if administered to rats, EEP increases locomotor activity, and decreases immobility in the Porsolt swim test. Regional brain levels of EEP are also markedly increased by electroconvulsive shock, another similarity with TRH. There are very important differences, however, between the two peptides as mentioned above. EEP is not hydrolyzed by serum enzyme thyroliberinase so its bioavailability is not limited like TRH. Since EEP is not attacked by that enzyme, it has exceptionally good bioavailability. For example, parenteral administration of EEP to rats elicits regional brain increases ranging rom 4 fold to >100 fold. Also EEP does not elivate plasma levels of thyroid hormone, like TRH, which can be problematic.

Although TRH was reported to be neuroprotective (Faden et al., 1989), its vulnerability to hydrolysis in the bloodstream, limits its bioavailability. As noted, EEP is not degraded in the bloodstream, and has good bioavailability, and gains access to the eye as well as the central nervous system, as detailed in section on description of invention.

The information in the foregoing paragraphs indicates that the therapeutic potential of EEP is not limited by the bioavailability problems or other limiting factors that characterize TRH.

EEP has potential as treatment for diseases and injuries to the brain and spinal cord in the civilian sector, including: injuries to commercial and sport divers, as well as sport parachutists and victims of automobile accidents; degenerative diseases of the spinal cord, such as Amyotrophic Lateral Sclerosis and Multiple Sclerosis; neuronal degeneration due to traumatic brain injury, stroke, and degenerative brain diseases such as Parkinson's, Huntington's and Alzheimer's. EEP offers potential for treatment of epilepsy, as well. We believe that EEP also has therapeutic potential as an treatment for ophthalmologic conditions such as: retinal injury due to accidental laser exposure; glaucoma, temporal neuritis or retinitis pigmentosa; and as adjuvant therapy before, during and after cataract surgery or retinal photocoagulation treatments for either age-related macular degeneration or diabetic retinopathy.

The inventors have also discovered that EEP neuroprotective efficacy is enhanced by the co administration of SPBN. The tripeptide EEP, which acts, at least in part, by reducing glutamate receptor-mediated calcium influx, is significantly enhanced by the addition of free radical scavenger N-tert-butyl-(2 sulfophenyl)-nitrone (SPBN) which was previously unknown. Co-treatment with the neuroprotectant SPBN which acts via a different mechanism (e.g. free radical scavenger) synergizes with EEP, thereby enhancing its neuropotective properties. SPBN offers an ROS scavenging mechanism which differs from vitamin E and other endogenous compounds. The nitrones react covalently with ROS to form stable nitroxide and as such they differ from endogenous scavengers. SPBN has also been shown to be neuroprotective against glutamate-induced toxicity in cultured neurons as well as in several rodent models of cerebral ischemia. In the rat focal ischemia model, it is neuroprotective even when initiation of treatment was delayed. Therefore, it enhances efficacy of EEP when administered together.

The present compositions are of special value in seizures, global hypoxic ischemic insults, in hypoxia, alone or in combination with blood flow reduction (ischemia) as well as in cases of cardiac arrest and in cases of abrupt occlusion of cerebral arteries (stroke) and laser induced retinal injury.

One aspect of the present invention relates to pharmaceutical compositions for the purposes set out above, in which the active ingredient is a compound EEP or also known as PGLU-GLU-PRO-NH$_2$.

Another aspect of the present invention relates to pharmaceutical compositions for the purposes set forth above in which the active ingredients are the compound EEP and SPBN.

Those skilled in the art are well aware of the wide variety of organic and inorganic acids and bases that may be used to make pharmaceutically acceptable salts of pharmacologically active compounds.

The novel compositions may contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as starcheds, sugars, flavoring agents and preservatives and the like. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration, as eye drops, intranasal or rectal administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles, such as isotonic saline or buffered saline, glucose in saline, etc. with pharmaceutically acceptable diluents. For local application such as eye drops, agents might be administered as non-irratating ointments or salves. In addition, the compositions of the present invention may be formed as aerosols, for intranasal and like administration.

The active agents are relatively safe. For example, EEP has minimal efficacy as a releaser of thyroid stimulating hormone or triiodothyronine, compared to the effect of throtropin releaseing hormone.

The dosage range will depend on the method of administration and the age, size and condition of the patient as would be recognized by one of ordinary skill in the art. The active dose for humans is generally in the range of from 0.5–10 mg per kg body weight, in a regimen of four times per day, orally or parenterally. However, it is evident to the man skilled in the art that dosages would be determined by the attending physician, according to the disease to be treated, method of administration, patient's age, weight, contraindications and the like.

Toxicity has not been a problem with the nitrone SPBN in animal studies, unlike another nitrone, PBN, which was toxic in rodents at high doses (Haseloff et al., 1997). SPBN is soluble in aqueous solutions and could be delivered in the same vehicles and routes as are appropriate for delivery of EEP. SPBN may be given in doses up to 300 mg/kg, four times per day, orally or parenterally.

The invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

Experimental Procedure and Results

Having generally described this invention, a further understanding can be obtained by reference to certain specific examples which are provided herein for purposes of illustration only and are not intended to be limiting unless otherwise specified. In the paragraphs that follow, we will present data which strongly suggest that EEP and EEP+ SPBN have significant therapeutic potential.

EXAMPLES

Example 1

Accordingly, we tested it against glutamate-induced excitotoxicity in cultured fetal rat neurons (Koenig, Long & Meyerhoff, 1998) [see Appendix II] to demonstrate that EEP is neuroprotective. Primary cultures of neurons derived from the forebrains and spinal cords of E15 fetuses were prepared and maintained in culture for eight days. Neurotoxicity in response to a 30 min. exposure to 100 $\mu$M glutamate (Glu) ±EEP was assessed using a colorimetric (MTT) assay of mitochondrial succinate dehydrogenase activity. EEP was found to reduce Glu-induced neurotoxicity in a dose-dependent manner in both forebrain and spinal cord neurons. 500 $\mu$M EEP significantly reduced Glu-induced toxicity in spinal cord neurons by 20±2.0% (n=7) and in forebrain neurons by 29.8±5.6% (n=7). A two-fold increase in EEP to 1 mM resulted in almost doubling the neuroprotection: 38.9±4.9% (n=8) in spinal neurons and 54.1±5.3% (n=7) in neurons from forebrain (see FIG. 1, Appendix III). Extending these observations, we compared the neuroprotective efficacy of EEP and TRH. We found that EEP was over three times as effective as TRH (see FIGS. 1 & 2, Appendix III).

Example 2

We have previously demonstrated that TRH inhibited glutamate-induced elevations in intracellular calcium (Koenig, Yourick & Meyerhoff, 1996), and proposed that this might be the mechanism of neuroprotective effects. Accordingly, having confirmed our initial hypothesis that EEP was neuroprotective, we examined the hypothesis that it would affect glutamate-induced calcium flux in a manner similar to TRH. We found, however, that pre-incubation with EEP does not affect glutamate-stimulated $Ca^{2+}$ dynamics, whereas TRH clearly does, demonstrating that EEP acts via a different mechanism than TRH. This is consistent with the reported low affinity of EEP for the TRH receptor. Conversely, TRH has relatively little effect on glutamate-mediated neurotoxicity, whereas EEP has neuroprotective properties. The evidence collected to date suggests that these two tripeptide analogs, which differ only in the middle amino acid, act in very different ways. In summary EEP has three times the neuroprotective potency of TRH and also has very good bioavailability. Accordingly, there is every reason to expect that EEP will be clinically effective as a neuroprotectant.

Example 3

TRH analog p-GLU-GLU-PRO-$NH_2$ (EEP) is neuroprotective in cultured neurons derived from the forebrains and spinal cords of fetal rats (Soc. Neurosci. Abstr. 14, 459, 1998). Moreover, it is more neuroprotective than TRH. The tripepide, which differs from TRH only in the substitution of GLU for HIS as the middle amino acid, is found in the brain (principally in the hippocampus and brain stem). As with TRH, EEP levels increase in specific brain regions in response to seizures (Pekary et al., Pep6des 20:107–119, 1999). The parallel increases in activity have led us to hypothesize that, like TRH, EEP may be an endogenous neuroprotectant. It has been found that the tripeptide has neuroprotective effects in rabbit retinal neurons exposed to ischemic conditions. Neurons acutely isolated from adult rabbit retinas were treated with 5 mM KCN and 10 mM 2-deoxyglucose to simulate ischemic conditions. EEP at 30 $\mu$M and 100 $\mu$M was added to some of the neuronal preparations. The bathing medium was removed after a 1 h exposure, and neuronal viability was assessed using the colorimetric dye MTT as an indicator of succinate dehydrogenase activity in viable neurons. Relative to controls, only 39.9% of the neurons exposed to chemical ischemia remained viable, whereas those simultaneously treated with EEP showed greater viability. 30 μM EEP resulted in the survival of 58.7 t: 7.9% of the neurons, and co-treatment with 100 gM EEP prevented all injury (109.4±16.6% of controls). These data indicate that EEP has potential for therapeutic use in ophthalmology against neurodegenerative diseases of the eye, such as diabetic neuropathy, age-related macular degeneration and glaucoma, as well as against laser-induced retinal damage, Example 4

The neuroprotective efficacy of the tripeptide, which acts, at least in part, by reducing glutamate receptor-mediated calcium influx, is significantly enhanced by the addition of the free radical scavenger N-tert-butyl-(2-sulfophenyl)-nitrone (SPBN). Treatment of cultured forebrain neurons (7–10 days in vitro) with EEP at different concentrations plus SPBN (10 mM) results in much greater viability in neurons subsequently exposed to Glu (100 μM, 1 h) than in those pre-treated with the same concentrations of EEP alone. The enhanced neuroprotection is especially evident at lower EEP concentrations. At concentrations of 30 μM and 100 μM, EEP alone is not protective; when SPBN is present with the EEP, the percentage neuroprotection is measured as 37.1 and 38.3 percent respectively. Neuroprotection evident at higher concentrations of the tripeptide is further enhanced by the addition of the nitrone. Percent neuroprotection=100× ((viability$_{test}$-viability$_{mean\ Glu}$))/(viability$_{mean\ control}$-viability$_{mean\ Glu}$)). Neuroprotection was then assessed by conducting the colorimetric MTT assay. SPBN significantly increased the neuroprotective efficacy of EEP at all of the four EEP concentrations tested. See Table A

TABLE A

| Dose | Percent Neuroprotection |
| --- | --- |
| EEP 30 μM | −1.205 ± 2.491 |
| EEP 30 μM + SPBN | 37.141 ± 5.441 |
| EEP 100 μM | −0124 ± 8.020 |
| EEP 100 μM + SPBN | 38.326 ± 8.686 |
| EEP 300 μM | 13.321 ± 7.319 |
| EEP 300 μM + SPBN | 44.850 ± 7.013 |
| EEP 1000 μM | 35.784 ± 15.431 |
| EEP 1000 μM + SPBN | 56.200 ± 4.109 |

The results clearly demonstrate that the compounds of the instant invention, namely EEP alone or EEP+SPBN, possess valuable neuroprotective properties.

References

Ashworth, R. J., Visser, T. J. and Cockle, S. M. The TRH-like peptide Pglu-GLU-PRO-NH2 is present in the porcine pituitary but not in reproductive tissues. Biochem. Biophys. Res. Commun. 181(3):1557–1563, 1991.

Back, T., Kohfio, K. and Hossmann, K.-A. J. Cereb. Blood Flow Metab. 14:12–19, 1994.

Cockle, S. M., Prater, G. V., Thefiord, C. R., Hamilton, C., Malone, P. R. and Mundy, A. R. Peptides related to thyrotropin-releasing hornlone (TRI-I) in human prostate and semen. Biochim. Biophys. Acta 1227:60–66,1994.

Faden, A. I., Vink, ILandMcIntos~ T. K. Th~otropin-releasinghormoneandcentral ne~oussystemtrauma. In Thyrotropin-Releasing Hormone: Biological Significance, edited by G. Metcalf and I. M. D. Jackson, Annals of the New York Academy of Sciences, 553:380–384, 1989.

H. D. Hacker, M. K. Koenig, D. L. Yourick, J. L. Meyerhoff NAAG protects against ischemia simulated by NaCN and 2-deoxyglucose in dissociated retinal cells. Neurosci. Abs. 24:1998.

Klootwijk, W., Sleddens-Linkels, E., de Boer, R. D. H., Jansen, C. A., Autar, R., de Herder, W. W., Boeve, E. R., Visset, T. J. and de Crreef, W. J. Renal clearance of the Thyrotropin-releasing hormone-like peptide pyroglutamyl-glutamyl-prolineamide in humans. J. Clin. Endo. Metab. 82(9):3068–3073, 1997.

Koenig, M. L., Yourick, D. L. and Meyerhoff, J. L. Thyrotropin-releasing hormone (TRH) inhibits glutamate-stimulated increases in intraneuronal calcium. Brain Research 730:143–149, 1996.

M. L. Koenig, J. B. Long, and J. L. Meyerhoff. Neuroprotection by the TRH-Like peptide pGLU-GLU-PRO-NH$_2$ (EEP). Neurosci. Abs 24:1998.

Kubek, M. J., Low, W. C., Sattin, A., Morzorati, S. L., Meyerhoff, J. L. and Larsen, S. H. Role of TRH in seizure modulation. In Thyrotropin-Releasing Hormnone: Biological Significance, edited by G. Metcalf and I. M. D. lackson, Annals of the New York Academy of Sciences, 553:286–303, 1989.

Lloyd, R. L., Pekary, A. E. and Sattin, A. Antidepressant effects of a stable analogue of thyrotropin releasing hormone in a rodent model of depression. Neurosci. Abstr. 23:1661, 1997

Long, J. B. et al. Dynorphin A-induced rat spinal cord injury: evidence for excitatory amino acid involvement in a pharmacological model of ischemic spinal cord injury. J. Pharm. Exp. Ther. 269(1):358–366, 1994.

Long et al., Laser-doppler fiowmetry measurements of subcortical blood flow changes after fluid percussion brain injury in rats. J. Neurotrauma 13(3): 149–162, 1996.

J. B. Long, J. L. Meyerhoffand B. S. Slusher. NAALADase inhibition protects against dynorphin A-induced ischemic spinal cord injury in rats. Neurosci. Abs. 23:2301, 1997.

Lumley, L. A., Hebert, M. A., Sipos, M. L. and MeyerholT, J. L. Evidence for long term behavioral effects of acute defeat. Neurosci. Abs. 22:461, 1996.

Meyerhoff, J. L., Lenox, R. H., Brown, P. V. and Gandhi, O. P. Inactivation of rodent brain enzymes in vivo. Proceedings of the I.E.E.E. 68(1):155–159, 1980.

Meyerhoff, J. L., Bates, V. E. and Kubek, M. J. Increases in brain thyrotropin-releasing hormone (TRH) following kindled seizures. Brain Research 525:144–148, 1990.

Pekary, A. E., Lloyd, R. and Sattin A. Electroconvulsive seizures (ECS) increase Pglu-GLU-PRO-NH2 (EEP) levels in rat limbic system. Neurosci. Abstr. 23:2377, 1997

Pekary, A. E., Sattin, A. and Lloyd, R. L. Electroconvulsive seizures increase levels of pGLU-GLU-PRO-NH2 (EEP) in rat brain. (in press, 1998).

Salazar, A. M., Jabbad, B., Vance, S. C., Grafman, J., Amin, D. and Dillon, I. D. Epilepsy after penetrating head injury. I. Clinical correlates: A report of the Vietnam Head Injury Study. Neurology 35:1406–1414, 1985.

Sattin, A., Hill, T. G., Meyerhoff, J. L., Norton, J. A. and Kubek, M. J. The prolonged increase in thyrotropin-releasing hormone in rat limbic forebrain regions following electroconvulsive shock. Regulatory-Peptides 19: 13–22, 1987.

Sato M, Morimoto K, & Wada I A: Antiepileptic effects ofthyrotropin-releasing hormone and new derivative, DN-1417, examined in feline amygdaloid kindling preparation. Epilepsia 25:537–544, 1984.

Tricklebank, M. D., Singh, L., Oles, R. J., Preston, C. and Iversen, S. D. The behavioral effects ofMK-801: a comparison with antagonists acting non-competitively and competitively at the NMDA receptor. Eur. J. Pharmacol. 167:127–135, 1989.

Vinding T. Age-related macular degeneration. Acta Ophthalmologica Scandinavica Suppl. 217:1–32,1995.

Neuroprotection by EEP in acutely isolated retinal neurons exposed to "chemical ischemia."

Having now fully described the invention, it will be apparent to one of ordinary skill in the art that many changes and modifications can be made thereto without departing from the spirit or scope of the invention as set for the herein.

What is claimed is:

1. A pharmaceutical composition comprising pGLU-GLU-PRO-$NH_2$ and one or more nitrones as active ingredients.

2. A pharmaceutical composition comprising pGLU-GLU-PRO-$NH_2$ and N-tert-Butyl-α-(2-sulfophenyl)nitrone as active ingredients.

3. A method of reducing Glu induced neurotoxicity in brain, spinal cord and/or retina comprising administering to a patent a composition comprising a therapeutically effective amount of pGLU-GLU-PRO-$NH_2$ as an active ingredient under time and conditions to treat said Glu induced neurotoxicity.

4. The method of claim 3, wherein said administering comprises administering to said patient the composition via oral, parenteral, intravenous, intramuscular, subcutaneous, transdermal, intrathecal, rectal or intranasal routes.

5. A method of reducing Glu induced neurotoxicity in brain, spinal cord and/or retina comprising administering to a patient a composition comprising a therapeutically effective amount of (a) pGLU-GLU-PRO-$NH_2$ and (b) N-tert-Butyl-α-2-sulfophenyl) nitrone or a free radical scavenging nitrone that enhances the effects of pGLU-GLU-PRO-$NH_2$ under time and conditions to treat said Glu induced neurotoxicity.

6. The method of claim 5, wherein said administering comprises administering to said patient the composition via oral, parenteral, intravenous, intramuscular, subcutaneous, transdermal, intrathecal, rectal or intranasal routes.

7. A method of protecting against Glu induced neurotoxicity in the brain, spinal cord and/or retina comprising administering to a patient a composition comprising a therapeutically effective amount of pGLU-GLU-PRO-$NH_2$ as an active ingredient under time and conditions to protect against said Glu induced neurotoxicity.

\* \* \* \* \*